US012577520B2

(12) United States Patent
Feng et al.

(10) Patent No.: US 12,577,520 B2
(45) Date of Patent: Mar. 17, 2026

(54) HIGH-PRESSURE ENVIRONMENT BIOLOGICAL ENRICHMENT AND SPRAY-TYPE SOLID ISOLATION AND CULTIVATION DEVICE

(71) Applicants:GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

(72) Inventors: Jingchun Feng, Guangdong (CN); Si Zhang, Guangdong (CN); Zhifeng Yang, Guangdong (CN); Yi Wang, Guangdong (CN); Yanpeng Cai, Guangdong (CN); Song Zhong, Guangdong (CN)

(73) Assignees: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

( * ) Notice: Subject to any disclaimer, the term of this patent is extended or adjusted under 35 U.S.C. 154(b) by 539 days.

(21) Appl. No.: 18/019,781

(22) PCT Filed: Mar. 30, 2022

(86) PCT No.: PCT/CN2022/084116
§ 371 (c)(1),
(2) Date: Feb. 3, 2023

(87) PCT Pub. No.: WO2023/173494
PCT Pub. Date: Sep. 21, 2023

(65) Prior Publication Data
US 2025/0101362 A1     Mar. 27, 2025

(30) Foreign Application Priority Data
Mar. 17, 2022     (CN) .......................... 202210264688.9

(51) Int. Cl.
C12M 1/34          (2006.01)
C12M 1/00          (2006.01)
C12M 1/26          (2006.01)

(52) U.S. Cl.
CPC ............ *C12M 41/40* (2013.01); *C12M 23/40* (2013.01); *C12M 23/58* (2013.01); *C12M 29/08* (2013.01); *C12M 33/04* (2013.01)

(58) Field of Classification Search
CPC ...... C12M 41/40; C12M 23/40; C12M 23/58; C12M 29/08; C12M 33/04; C12M 1/00;
(Continued)

(56) References Cited

U.S. PATENT DOCUMENTS 10,379,016  B1     8/2019   Alam
2022/0198962  A1*   6/2022   Zhang ................... G09B 23/40

FOREIGN PATENT DOCUMENTS

CN          205893276          1/2017
CN          108179100          6/2018
(Continued)

OTHER PUBLICATIONS

Ziqiang Meng, "Ecotoxicology", China Environmental Publishing Group, with English translation thereof, Sep. 30, 2019, pp. 1-7.
(Continued)

*Primary Examiner* — William H. Beisner
*Assistant Examiner* — Danielle B Henkel
(74) *Attorney, Agent, or Firm* — JCIPRNET

(57)          ABSTRACT
The invention proposes a high-pressure environment biological enrichment and spray-type solid isolation and cultivation device, including a spray-type isolation and cultiva-
(Continued)

tion solid unit, and a biological enrichment unit. In the case of constructing a high-pressure, low-temperature environment consistent with the marine environment, the biological enrichment unit is used to realize enrichment and multi-stage purification process of marine microorganisms, obtain a biological enrichment fluid and inject the biological enrichment fluid into the spray-type isolation and cultivation solid unit; and the spray-type isolation and cultivation solid unit is use to convert the biological enrichment fluid into a state of microbeads, so that the biological enrichment fluid can be isolated and cultivated in a dispersed state.

9 Claims, 5 Drawing Sheets

(58) Field of Classification Search
CPC . C12M 1/02; C12M 1/04; C12M 1/26; C12M 1/34; C12M 1/36; C12M 1/38
See application file for complete search history.

(56) References Cited

FOREIGN PATENT DOCUMENTS

| CN | 208098019 | | 11/2018 | |
| CN | 109845634 A | * | 6/2019 | |
| CN | 110777061 | | 2/2020 | |
| CN | 210974632 | | 7/2020 | |
| CN | 111551390 | | 8/2020 | |
| CN | 213951199 | | 8/2021 | |
| CN | 113549545 A | * | 10/2021 | ........... C12M 41/12 |
| CN | 114127248 | | 3/2022 | |
| JP | S63267262 | | 11/1988 | |

OTHER PUBLICATIONS

Haijin Mou et al., "Marine Microbial Engineering", Ocean University of China Press, with English translation thereof, Jul. 31, 2016, pp. 1-8.
Shi-Lun Li et al., "Control system of simulating platform for deep-sea extreme environment", Journal of Zhejiang University, with English abstract, Nov. 30, 2005, pp. 1-4.
Jian-Wen Zhang et al., "Communication Protocol and Realization for Temperature Controller of Simulated Platform in Extrem Environment", Mechanical & Electrical Engineering Magazine, with English abstract, Dec. 31, 2004, pp. 1-3.
"International Search Report (Form PCT/ISA/210) of PCT/CN2022/084116," mailed on Dec. 15, 2022, pp. 1-5.

* cited by examiner

HIGH-PRESSURE ENVIRONMENT BIOLOGICAL ENRICHMENT AND SPRAY-TYPE SOLID ISOLATION AND CULTIVATION DEVICE

CROSS-REFERENCE TO RELATED APPLICATION

This is a 371 application of the International PCT application serial no. PCT/CN2022/084116, filed on Mar. 30, 2022, which claims the priority benefits of China Application No. 202210264688.9, filed on Mar. 17, 2022. The entirety of each of the above-mentioned patent applications is hereby incorporated by reference herein and made a part of this specification.

TECHNICAL FIELD

The invention relates to the technical field of marine microorganisms, and in particular, to a high-pressure environment biological enrichment and spray-type solid isolation and cultivation device.

DESCRIPTION OF RELATED ART

High-pressure habitats account for a large proportion of the earth, and habitats with a pressure greater than 30 MPa are widely distributed in the marine environment, and more than 77% of the marine environment has a water depth of more than 3000 meters. Deep-sea sediments, deep-sea basins, trenches, and deep terrestrial layers are all high-pressure environments. Microbes in high-pressure habitats changed with depth, salinity, pH, oxygen content, and nutrients, showing significant diversity. However, since the existing microbial enrichment and isolation and cultivation technologies are mainly carried out in the atmospheric environment, especially the solid isolation and cultivation technology lacks the precedent for the use of high-pressure environment, resulting in that now only less than 10% of microorganisms in high-pressure environment have been pure cultivated, which brings difficulties to the correct understanding of the phenotype, genes, and functional development and utilization value of these microorganisms.

The prior art discloses a deep-sea microorganism cultivation cabin including: a linear bearing, a tension spring, a pressure compensation cavity, a fixed top plate, a deep-sea motor assembly, a fixed bottom plate, a hose and a cultivation cabin body; this solution uses the deep-sea motor assembly to open an end cap of the cultivation cabin body, and conducts microbial enrichment cultivation in a fully open state, during the deployment and recovery process, the end cap of the cultivation cabin body is closed to seal the microorganism cultivation cabin. Although deep-sea in-situ microbial enrichment cultivation can be achieved, marine microorganisms are not subject to isolation and cultivation, which cannot effectively improve the success rate of cultivation.

SUMMARY

In order to solve at least one of the above technical deficiencies, the invention provides a high-pressure environment biological enrichment and spray-type solid isolation and cultivation device. By reshaping its in-situ environment to carry out enrichment cultivation and isolation of marine microorganisms, the cultivability of the marine microorganisms is improved, a pure cultivation technology is formed, and an important basic means is provided for the development and utilization of high-pressure environment microbial resources.

In order to solve to above technical problem, the technical solution of the invention is as follows.

The present solution proposes a high-pressure environment biological enrichment and spray-type solid isolation and cultivation device, including a spray-type isolation and cultivation solid unit, a biological enrichment unit, a pressurization system, a temperature environment control system and a control-acquisition terminal. In particular, the biological enrichment unit is used to realize enrichment and multi-stage purification process of marine microorganisms, obtain a biological enrichment fluid and inject the biological enrichment fluid into the spray-type isolation and cultivation solid unit. The spray-type isolation and cultivation solid unit is use to convert the biological enrichment fluid into a state of microbeads, so that the biological enrichment fluid can be isolated and cultivated in a dispersed state, and culturability of the marine microorganisms is effectively improved. The pressurization system and the temperature environment control system are both connected to the spray-type isolation and cultivation solid unit and the biological enrichment unit respectively, for constructing a high-pressure, low-temperature environment consistent with the marine environment within the biological enrichment unit and the spray-type isolation and cultivation solid unit, ensuring that enriched deep-sea microorganisms are enriched, purified, isolated and cultivated under in-situ environmental conditions. Both a control terminal and a signal detection terminal of the spray-type isolation and cultivation solid unit and a control terminal and a signal detection terminal of the biological enrichment unit are electrically connected to the control-acquisition terminal.

In the above solution, the biological enrichment unit can realize in-situ enrichment cultivation of the microorganisms under temperature and pressure environmental conditions in the ocean, and the spray-type isolation and cultivation solid unit can convert the biological enrichment fluid into the state of microbeads, so that the biological enrichment fluid can be isolated and cultivated in the dispersed state. By reshaping its in-situ environment, to carry out enrichment cultivation and isolation of marine microorganisms, the problem of isolation and pure cultivation of the marine microorganisms in high-pressure environment is solved, the cultivability of the marine microorganisms is improved, a pure cultivation technology is formed, and an important basic means is provided for the development and utilization of high-pressure environment microbial resources.

In the above solution, the control-acquisition terminal includes a data acquisition device, a data central processing unit, an operating computer and the like to realize the monitoring of various environmental data information changes during the enrichment, isolation and purification of microbial enrichment bacteria in a high-pressure environment, and functions such as real-time acquisition, processing, storage and image output.

In particular, the spray-type isolation and cultivation solid unit includes a spray-type isolation and cultivation chamber, a liquid injection module, an environmental parameter monitoring unit, a microporous nozzle, a gas injection valve and a gas outlet valve. In particular, the spray-type isolation and cultivation chamber is internally provided with a solid culture plate, for isolating and culturing the microorganisms. The spray-type isolation and cultivation chamber is placed in the temperature environment control system, and the temperature environment control system ensures that a temperature in the spray-type isolation and cultivation chamber is kept constant and consistent with a submarine temperature of a deep-sea cold spring area. The environmental parameter monitoring unit is used to monitor temperature and pressure changes inside the spray-type isolation and cultivation chamber, and transmit data to the control-acquisition terminal. The microporous nozzle is disposed inside the spray-type isolation and cultivation chamber, and is connected to the liquid injection module disposed outside the spray-type isolation and cultivation chamber. An input end of the liquid injection module is connected to a liquid output end of the biological enrichment unit, for injecting the biological enrichment fluid into the spray-type isolation and cultivation chamber, after passing through the microporous nozzle, the biological enrichment fluid will be dispersed into the state of microbeads scattered on the solid culture plate. The gas injection valve and the gas outlet valve are both disposed on the spray-type isolation and cultivation chamber, the gas injection valve is connected to the pressurization system, for injecting a gas into the spray-type isolation and cultivation chamber to increase an internal pressure thereof; and a control terminal of the gas outlet valve is electrically connected to the control-acquisition terminal, for controlling the gas to be discharged from the spray-type isolation and cultivation chamber to reduce the internal pressure thereof.

In particular, the liquid injection module includes a microflow pump, a liquid injection port and a liquid delivery pipeline. In particular, an input end of the microflow pump is connected to the liquid output end of the biological enrichment unit, and an output end of the microflow pump is connected to the liquid injection port by the liquid delivery pipeline. The liquid injection port is connected to the microporous nozzle.

In particular, the spray-type isolation and cultivation chamber is provided with a quick-opening clamp.

In the above solution, by applying the principle of spray-type isolation, the spray-type isolation and cultivation chamber involved is provided in this solution, to inject the microbial enrichment cultivation solution of the biological enrichment unit into the spray-type isolation and cultivation chamber through the microflow pump, via the microporous nozzle, the microbial enrichment cultivation solution is dispersed into an ultramicro strain, scattering on a solid medium, and after a single tiny droplet that is small enough is attached to the solid medium, the process of isolation and cultivation will be realized. The spray-type isolation and cultivation chamber involved in this solution is provided with a liquid injection port, which is used to inject a microbial enrichment bacteria solution into the spray-type isolation and cultivation chamber. The spray-type isolation and cultivation chamber is further provided with the gas injection valve, which is used to inject a gas needed for growth of the microorganisms or an inert gas into the spray-type isolation and cultivation chamber to pressurize the cultivation chamber. A high-strength solid culture plate is placed inside the spray-type isolation and cultivation chamber, which is used to fill the solid medium to meet the needs of the implantation and growth of the microorganisms. Inside the spray-type isolation and cultivation chamber, it is provided with a key component to disperse the bacteria solution: the microporous nozzle, which can be spherical, trumpet-shaped or lotus-shaped, etc., so that the microbial enrichment bacteria solution can be dispersed into uniform fine droplets in a high-pressure environment after coming out of the liquid injection port. The pore size on the nozzle is fine enough and sufficient, so that the bacteria solution can be isolated and grown after being sprayed. The distance between the microporous nozzle and the solid culture plate should be such that the sprayed bacteria solution just adheres to the solid culture plate evenly, and will not be scattered on an inner wall of the spray-type isolation and cultivation chamber.

In particular, the biological enrichment unit consists of a plurality of high-pressure microbial enrichment cultivation kettles connected in series. A removable sealing lid and a connecting sampling valve group are provided on the high-pressure microbial enrichment cultivation kettle which is internally provided with a temperature and pressure sensor group. Each of the high-pressure microbial enrichment cultivation kettles is disposed in the temperature environment control system. In particular, the removable sealing lid is used to facilitate the sterilization operation inside the high-pressure microbial enrichment cultivation kettle and put into the cultivation substrate. The connecting sampling valve group is used for connection and sampling of each of the high-pressure microbial enrichment cultivation kettles, the connecting sampling valve group is connected to the pressurization system, for feeding a liquid or a gas into the high-pressure microbial enrichment cultivation kettle to increase a pressure in the high-pressure microbial enrichment cultivation kettle, making a pressure value in the high-pressure microbial enrichment cultivation kettle consistent with an actual situation in a deep sea. The temperature and pressure sensor group is used to monitor temperature and pressure changes in the high-pressure microbial enrichment cultivation kettle in real time, and send a signal to the control-acquisition terminal.

In particular, a stirring rod is provided on the high-pressure microbial enrichment cultivation kettle. The stirring rod is used for the high-pressure microbial enrichment cultivation kettle to enhance a reaction process of a substrate during a cultivation process.

In the above solution, the high-pressure microbial enrichment cultivation kettle is designed with the stirring rod on the top, which can enhance mass transfer by manual or mechanical stirring, enhance the reaction process of the substrate during the cultivation process, and increase the energy and nutrient utilization efficiency of the microorganisms.

In particular, the connecting sampling valve group includes a liquid inlet valve, a gas inlet valve, a sampling valve, a gas releasing valve and a liquid outlet valve. In particular, the high-pressure microbial enrichment cultivation kettles are connected in series through the liquid outlet valve and the liquid inlet valve, the liquid outlet valve of the former high-pressure microbial enrichment cultivation kettle is connected to the liquid inlet valve of the latter high-pressure microbial enrichment cultivation kettle. The gas inlet valve is used to input gas into the high-pressure microbial enrichment cultivation kettle to increase the pressure in the high-pressure microbial enrichment cultivation kettle, making the pressure value in the high-pressure microbial enrichment cultivation kettle consistent with the actual situation in the deep sea. The gas releasing valve is used to release the gas in the high-pressure microbial enrichment cultivation kettle to reduce the pressure in the high-pressure microbial enrichment cultivation kettle, and a control terminal thereof is electrically connected to the control-acquisition terminal. The sampling valve is used to conduct real-time sampling analysis of the microorganisms in the high-pressure microbial enrichment cultivation kettle.

In the above solution, the high-pressure microbial enrichment cultivation kettle is provided with the sampling valve, which is used to analyze and detect samples during the enrichment process, so as to adjust the corresponding environmental parameters and optimize the enrichment cultivation process.

In the above solution, the plurality of the high-pressure microbial enrichment cultivation kettles consist the biological enrichment unit, the bacteria solution in the former high-pressure microbial enrichment cultivation kettle is transferred to the latter high-pressure microbial enrichment cultivation kettle by holding pressure, and so on, the bacteria solution is diluted according to the concentration gradient, the microbial bacteria solution obtained in the final-stage high-pressure microbial enrichment cultivation kettle will supply the enriched and highly purified functional microorganisms under the stress of the nutrient conditions under the high-pressure environment. The pressure-holding transfer can be realized by taking out the enrichment liquid in the former high-pressure microbial enrichment cultivation kettle through the sampling valve and pumping it into the latter high-pressure microbial enrichment cultivation kettle through the micro-injection pump. The pressure of the latter high-pressure microbial enrichment cultivation kettle may also be pressurized to slightly less than the previous high-pressure microbial enrichment cultivation kettle, and then the liquid outlet valve of the previous high-pressure microbial enrichment cultivation kettle and the liquid inlet valve of the latter high-pressure microbial enrichment cultivation kettle can be opened, the microbial enrichment fluid will automatically enter into the later high-pressure microbial enrichment cultivation kettle from the later high-pressure microbial enrichment cultivation kettle for purification and cultivation under the condition of slight pressure difference. During the whole process of multi-enrichment and liquid isolation and purification cultivation, the temperature and pressure environmental conditions of the high-pressure microbial enrichment cultivation kettle are consistent with the environmental conditions of the microorganisms in the deep sea, ensuring the effectiveness of enrichment cultivation.

In particular, the temperature environment control system includes a low/high temperature environment system, a refrigerating/heating system and a water bath temperature monitoring system. The spray-type isolation and cultivation solid unit and the biological enrichment unit are both disposed in the low/high temperature environment system for a water bath, and the low/high temperature environment system is connected to the refrigerating/heating system to realize heat exchange. The water bath temperature monitoring system is used to monitor temperature and pressure changes in the low/high temperature environment system, and transmit monitoring data to the control-acquisition terminal. A control terminal of the refrigerating/heating system is electrically connected to the control-acquisition terminal.

In the above solution, the maintenance of the constant temperature conditions of the spray-type isolation and cultivation chamber and the high-pressure microbial enrichment cultivation kettle is mainly to place the spray-type isolation and cultivation chamber and the high-pressure microbial enrichment cultivation kettle in the low/high temperature environment system monitoring the temperature for the water bath, and through the heat exchange with the low/high temperature environmental system, the constant temperature state in the spray-type isolation and cultivation chamber and the high-pressure microbial enrichment cultivation kettle is maintained. Or the spray-type isolation and cultivation chamber and the high-pressure microbial enrichment cultivation kettle are placed in an air heat exchange constant temperature room.

The temperature conditions in the spray-type isolation and cultivation chamber and high-pressure microbial enrichment cultivation kettle involved in the above solution are mainly controlled by the low/high temperature environment system. For example, a ring-wall cavity of the spray-type isolation and cultivation chamber and a ring-wall cavity of the high-pressure microbial enrichment cultivation kettle are injected with a cold/hot fluid, by circulating cooling or heating the fluid, the low temperature or high temperature state of the fluid in the ring-wall cavity is ensured, and then by the heat exchange between the cold/hot fluid and the built-in cavity, the low temperature or high temperature state in the built-in cavity is ensured. Or the spray-type isolation and cultivation chamber and the high-pressure microbial enrichment cultivation kettle are placed in a low temperature/high temperature water bath/oil bath environment, special temperature conditions required in the spray-type isolation and cultivation chamber and the high-pressure microbial enrichment cultivation kettle are ensured. Or the spray-type isolation and cultivation chamber and the high-pressure microbial enrichment cultivation kettle are placed in a cooling/heating room or box with a constant temperature guaranteed by air heat exchange. Some extreme temperature conditions can be maintained by using several temperature control methods mentioned above at the same time. It monitors the temperature in real time through the environmental parameter monitoring unit and the temperature and pressure sensor group.

In particular, the pressurization system includes an air compressor, a booster pump, a gas storage tank, a pressure regulating valve and a ventilation pipeline. In particular, the air compressor, the booster pump, the gas storage tank and the pressure regulating valve are connected in sequence through the ventilation pipeline, and finally are connected to the spray-type isolation and cultivation solid unit and the biological enrichment unit in sequence through the ventilation pipeline, for injecting a gas into the spray-type isolation and cultivation solid unit and the biological enrichment unit for pressurization. The pressure regulating valve is used to regulate an internal pressure of the spray-type isolation and cultivation solid unit and the biological enrichment unit. A control terminal of the air compressor, a control terminal of the booster pump and a control terminal of the pressure regulating valve are all electrically connected to the control-acquisition terminal.

The pressurization system involved in the above solution is mainly used to inject the gas into the high-pressure microbial enrichment cultivation kettle and the spray-type isolation and cultivation chamber for pressurization, so that pressure environment in the high-pressure microbial enrichment cultivation kettle and the spray-type isolation and cultivation chamber is consistent with the pressure value of the microorganisms in the ocean in-situ.

In the above solution, the pressure changes in the cultivation chamber are monitored in real time through the environmental parameter monitoring unit and the temperature and pressure sensor group, and by the pressurization and decompression of the cultivation chamber carried out through active inflation/deflation, the pressure value in the cultivation chamber is kept consistent with the marine environmental conditions for the growth of the microorganisms.

In particular, the high-pressure environment biological enrichment and the spray-type solid isolation and cultivation device further include a movable platform, and the spray-type isolation and cultivation solid unit, the biological enrichment unit, the pressurization system, the temperature environment control system and the control-acquisition ter-
minal are all disposed on the movable platform, for increas-
ing universality of cultivation scenarios.

Preferably, the spray-type isolation and cultivation solid
unit is provided with a plurality of the microporous nozzles
and a plurality of the solid culture plates. The liquid injection
module is connected to each of the microporous nozzles
simultaneously. The solid culture plates are disposed later-
ally at a bottom of the spray-type isolation and cultivation
solid unit to realize lateral isolation and cultivation of the
microorganisms under conditions of the same temperature
and same pressure.

Preferably, the spray-type isolation and cultivation cham-
ber is provided with a plurality of connecting partitions in a
vertical direction, partitioning the spray-type isolation and
cultivation chamber into a plurality of connecting cultivation
cavities. In particular, a solid culture plate is provided on
each of the connecting partitions, and the microporous
nozzle is provided inside each of the cultivation cavities.
The liquid injection module is connected to each of the
microporous nozzles simultaneously, realizing vertical iso-
lation and cultivation of the microorganisms under condi-
tions of the same temperature and same pressure.

Preferably, the spray-type isolation and cultivation solid
unit includes a plurality of the spray-type isolation and
cultivation chambers, each of the spray-type isolation and
cultivation chambers is provided with an independent
microporous nozzle, an independent solid culture plate and
an independent gas injection valve. All of the spray-type
isolation and cultivation chambers are placed in the same
temperature environment control system. The liquid injec-
tion module is connected to the microporous nozzle in each
of the spray-type isolation and cultivation chambers simul-
taneously, realizing isolation and cultivation of the micro-
organisms under conditions of the same temperature and
different pressures.

Preferably, the spray-type isolation and cultivation solid
unit includes a plurality of the spray-type isolation and
cultivation chambers, and each of the spray-type isolation
and cultivation chambers is provided with an independent
microporous nozzle, an independent solid culture plate and
an independent gas injection valve. Each of the spray-type
isolation and cultivation chamber is placed in an indepen-
dent temperature environment control system which is cor-
respondingly provided. The liquid injection module is con-
nected to the microporous nozzle in each of the spray-type
isolation and cultivation chamber simultaneously, and all of
the gas injection valves are in communication, realizing
isolation and cultivation of the microorganisms under con-
ditions of different temperatures and same pressure.

On the basis of the above solution, by cutting off the
communication between all the gas injection valves and
controlling them separately, isolation and cultivation of the
microorganisms under conditions of different temperatures
and different pressures can be realized.

In order to improve the screening efficiency of the micro-
organisms, the isolation process of the microorganisms in
the high-pressure environment involved in this solution uses
the single spray-type isolation and cultivation chamber for
multi-stage combined cultivation to form a cultivation pro-
cess. Under the same temperature and pressure environmen-
tal conditions, in order to increase the cultivation area and
the sorting volume, a plurality of solid culture plates can be
arranged in the lateral cultivation chamber, each solid cul-
ture plate can be filled with medium with different nutrients,
and each plate is provided with one microporous nozzle to
improve the efficiency of isolation and cultivation. It can also be arranged as a tower structure, where the plurality of
solid culture plates are combined with the microporous
nozzles for vertical stacking, or multiple groups can be
combined horizontally and vertically for large-scale culti-
vation. The entire spray-type isolation and cultivation cham-
ber is set to the same temperature and pressure environmen-
tal conditions. If in order to screen strains under different
environment conditions of pressure and temperature, differ-
ent spray-type isolation and cultivation chambers can also be
combined in parallel, the temperature and pressure environ-
ment of each spray-type isolation and cultivation chamber
can be controlled separately, and the temperature and pres-
sure parameters can be set gradiently according to the
sorting purpose. The plurality of the spray-type isolation and
cultivation chambers are combined in parallel and connected
to the microflow pump and the final-stage high-pressure
microbial enrichment cultivation kettle. The sorting process
is formed under different temperature and pressure environ-
mental conditions.

This solution improves the cultivability of microorgan-
isms by constructing a high-pressure environment for micro-
organisms in a high-pressure microorganism enrichment
cultivation kettle and a spray-type isolation and cultivation
chamber for microorganisms in a high-pressure environ-
ment, such as the high pressure and extreme temperature
environmental conditions of life in the marine environment.
Through multi-stage enrichment and liquid dilution cultiva-
tion, functional microorganisms with high purity under
directional environmental stress are obtained, and at the
same time, combined with spray-type solid cultivation iso-
lation, monoclonal microorganisms colonies are obtained.
The whole process of enrichment and isolation is carried out
under the in-situ pressure and temperature environment of
the microorganisms. At the same time, multiple sets of
isolation and cultivation chambers can be combined to form
an efficient isolation process with different medium combi-
nations.

The high-pressure environment marine microbial enrich-
ment cultivation and isolation technology involved in this
solution mainly includes two steps of enrichment and iso-
lation. First, through enrichment cultivation of the biological
enrichment unit, after obtaining the microflora with higher
purity, the microflora enter the spray-type isolation and
cultivation chamber under the condition of maintaining
pressure for solid cultivation and isolation, and through
simultaneously screening the combined process of different
cultivation medium and environmental conditions, a pure
cultivation strain is obtained. Specifically:

Enrichment Cultivation Process:

The first is to sterilize the high-pressure microbial enrich-
ment cultivation kettle and its accompanying pipes and
valves, the substrates to be cultivated, such as deep-sea
sediments, macrobiological tissues and extracts symbiotic
with microorganisms, are then loaded in sequence, the
nutrient solution required for cultivation is then loaded from
the liquid inlet valve, and then the gas required for the
cultivation (if it is not required, inert gas can be injected) is
injected from the gas inlet valve to increase the pressure
value in the high-pressure microorganism enrichment culti-
vation kettle to be consistent with the actual environmental
conditions in the deep sea. During the cultivation process,
the stirring rod on the top is used to increase the mass
transfer effect and optimize the cultivation process. After the
first-stage high-pressure microbial enrichment cultivation
kettle has completed the cultivation process, nutrient solu-
tion needed for cultivation is injected into the second-stage
high-pressure microbial enrichment cultivation kettle, and gas and the nutrient solution are injected into the second-stage high-pressure microbial enrichment cultivation kettle by the pressurization system for pressurization, the amount of the cultivation solution injected into the second-stage high-pressure microbial enrichment cultivation kettle needs to be based on the sorting requirements to ensure a dilution ratio of the concentration of the enrichment from the first-stage high-pressure microbial enrichment cultivation kettle into the second-stage high-pressure microbial enrichment cultivation kettle, and then the microbial bacteria solution in the first-stage high-pressure microbial enrichment cultivation kettle is transferred to the second-stage high-pressure microbial enrichment cultivation kettle through pressure-holding transfer. By that analogy, the microorganisms in the final-stage high-pressure microbial enrichment cultivation kettle will reach a highly purified state. When the concentration of deep-sea microbial bacteria solution in the final-stage high-pressure microbial enrichment cultivation kettle reaches more than 106 per mL, it can be considered that a better purification state has been achieved. For specific cultivated microorganisms, the dilution ratio of each stage can be adjusted.

When the concentration of the bacterial solution in the enrichment cultivation process has been identified to meet the requirements, it will enter into the solid isolation and cultivation process.

Solid Isolation and Cultivation Process:

The first is to sterilize the spray-type isolation and cultivation chamber and all its internal devices and related pipes and valves to keep them sterile. Then the plate is filled with the sterilized solid medium. In order to avoid the solid agar medium from liquefying or forming a porous structure under high pressure conditions, the solid culture plate can be filled with alumina powder, fine glass beads/steel balls, steel wire balls, etc. as a support to meet the needs of solid isolation and cultivation. Then the temperature environment control system is turned on to ensure that the temperature in the spray-type isolation and cultivation chamber is consistent with the temperature conditions of the microorganisms in the marine environment. Then gas is injected into the spray-type isolation and cultivation chamber through the gas injection valve for pressurization, so that the pressure conditions in the spray-type isolation and cultivation chamber are consistent with the pressure conditions of the microorganisms living in the marine environment. After ensuring that all system components are working properly, the microflow pump is turned on and the microbial enrichment fluid is injected into the spray-type isolation and cultivation chamber from the final-stage high-pressure microbial enrichment cultivation kettle, after the microbial enrichment fluid passes through the microporous nozzle, it will be divided into ultra-fine uniform droplets, and the ultra-fine droplets will be transported to the solid culture plate at the bottom of the spray-type isolation and cultivation chamber under the action of gravity. The ultra-fine droplets are implanted and grown in the solid medium, and after a sufficient incubation period, isolated single colonies will grow.

The automatic cultivation process of microorganisms involved in this solution mainly includes two conditions, the same temperature and pressure conditions and different temperature and pressure conditions. The same temperature and pressure conditions are mainly to meet the needs of large-scale simultaneous screening and isolation of different medium. First, in the spray-type isolation and cultivation chamber, several solid culture plates and microporous nozzles are placed in combination horizontally or vertically, all the inlets of the microporous nozzles are connected in parallel by pipeline and to the microinjection pump and the final-stage high-pressure microbial enrichment cultivation kettle. Different temperature and pressure conditions are mainly to combine different spray-type isolation and cultivation chambers in parallel, the temperature and pressure environment of each spray-type isolation and cultivation chamber are individually controlled, and the parameter conditions can be set in a gradient according to the sorting purpose. The plurality of the spray-type isolation and cultivation chambers are combined in parallel and connected to the microflow pump and the final-stage high-pressure microorganism enrichment cultivation kettle. When the whole process is assembled and debugged, all the cultivation chamber and the pipes and the valves involved in the cultivation process are sterilized as a whole. Then through temperature and pressure monitoring, it is ensured that the temperature and pressure environmental conditions in all spray-type isolation and cultivation chambers are consistent with the temperature and pressure environmental conditions of the marine environment where the microorganisms are located. The micro-injection pump is turned on, and the finely dispersed droplets will be implanted on the solid culture plate for isolation and cultivation, which can realize the automatic sorting process under different medium environments, and effectively ensure the isolation, cultivation and purification of the microorganisms in the high-pressure environment. Key technologies are provided for efficient utilization and sorting process of microorganisms in high-pressure environment.

The present invention mainly relates to the continuous enrichment, spray-type isolation and cultivation device and process of microorganisms under high-pressure environment, and proposes a cultivation device and technical method for multi-stage enrichment cultivation and multi-medium spray-type automatic isolation and purification of marine microorganisms under high pressure and extreme temperature environmental conditions.

This solution solves the problem that the existing indoor pure cultivation technology method is separated from the high pressure and extreme temperature environmental conditions for the survival of microorganisms, which leads to the poor survival activity of a large number of microorganisms and cannot achieve pure cultivation. This solution does not require professional operators, and can be used in multi-cultivation scenarios such as research laboratories and scientific research ships, and has wide adaptability.

This solution does not require manual enrichment and streak isolation operations by professionals, and can be enriched and sorted on a large scale, reducing labor costs, and realizing automated isolation and cultivation of high-pressure environment microorganisms under in-situ pressure and temperature environmental conditions. Under the high-pressure environment, pure cultivation of microorganisms in-situ provides an important technical means.

Compared with the existing pure cultivation technology, this solution proposes a high-pressure pure cultivation technology for enrichment and isolation and cultivation of microorganisms in extreme environmental conditions under high-pressure environment conditions, and solves the problem that the existing atmospheric isolation and cultivation technology is separated from the temperature and pressure environmental conditions of high-pressure environment microorganisms in-situ survival, resulting in poor activity of most microorganisms, or the phenotype is greatly different from the in-situ environmental conditions, and cannot be isolated and cultivated. Compared with the existing isolation and cultivation technology, this solution can effectively reduce the investment of professionals, and can carry out large-scale enrichment and isolation and cultivation, improve the screening efficiency of difficult-to-cultivate microorganisms, and improve the screening and cultivation efficiency of functional bacteria in high-pressure environment.

Compared with the prior art, the beneficial effects of the technical solution of the present invention are as follows:

The present invention proposes a high-pressure environment biological enrichment and spray-type solid isolation and cultivation device, through the biological enrichment unit, the enrichment cultivation of microorganisms under the temperature and pressure environment conditions of the ocean in-situ can be realized, and the spray-type isolation and cultivation solid unit can convert the biological enrichment fluid into the state of microbeads, so that the biological enrichment fluid can be isolated and cultivated in a dispersed state. In the present invention. By reshaping its in-situ environment to carry out enrichment cultivation and isolation of marine microorganisms, the problem of isolation and pure cultivation of the marine microorganisms in high-pressure environment is solved, the cultivability of the marine microorganisms is improved, a pure cultivation technology is formed, and an important basic means is provided for the development and utilization of high-pressure environment microbial resources.

Figure 1:
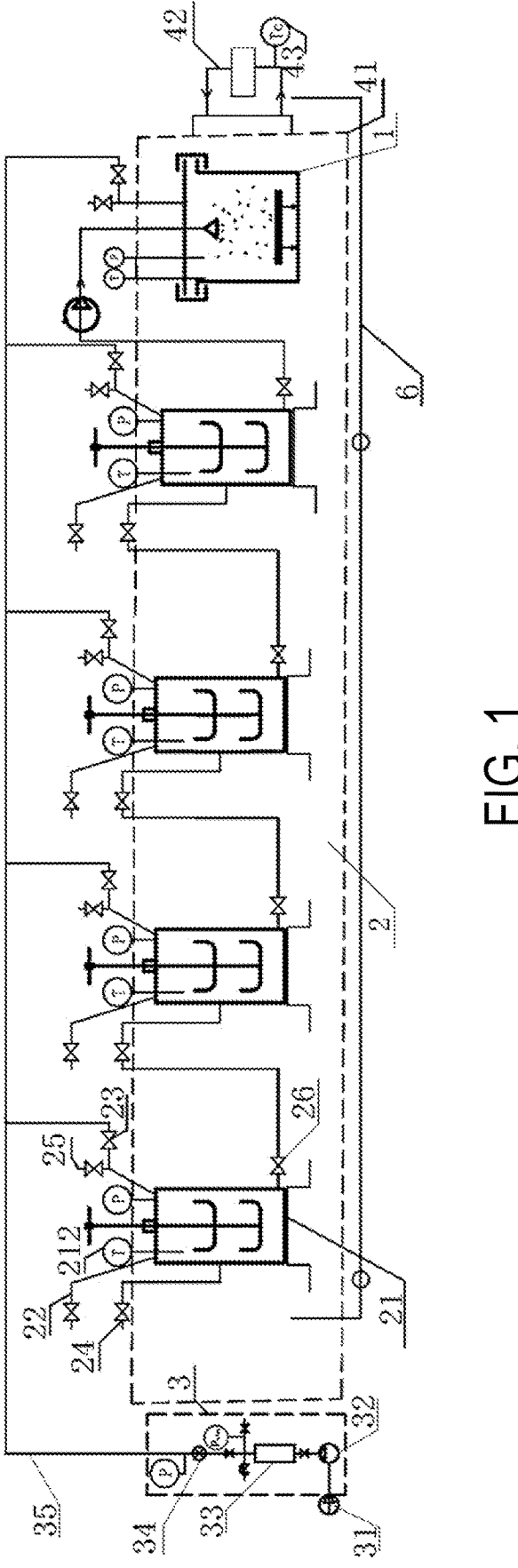
FIG. 1 is a schematic structural diagram of a device according to the present invention.

In the drawings: 1: spray-type isolation and cultivation solid unit; 11: spray-type isolation and cultivation chamber; 111: solid culture plate; 112: quick-opening clamp; 113: connecting partition; 114: cultivation cavity; 12: liquid injection module; 121: microflow pump; 122: liquid injection port; 123: liquid delivery pipeline; 13: environmental parameter monitoring unit; 14: microporous nozzle; 15: gas injection valve; 16: gas outlet valve; 2: biological enrichment unit; 21: high-pressure microbial enrichment cultivation kettle; 211: removable sealing lid; 212: temperature and pressure sensor group; 213: stirring rod; 22: liquid inlet valve; 23: gas inlet valve; 24: sampling valve; 25: gas releasing valve; 26: liquid outlet valve; 3: pressurization system; 31: air compressor; 32: booster pump; 33: gas storage tank; 34: pressure regulating valve; 35: ventilation pipeline; 4: temperature environment control system; 41: low/high temperature environment system; 42: refrigerating/heating system; 43: water bath temperature monitoring system; 5: control-acquisition terminal; 6: movable platform.

DESCRIPTION OF THE EMBODIMENTS

The accompanying drawings are for illustrative purposes only and should not be construed as limitations on this application.

This embodiment is a complete usage example with rich content.

In order to better illustrate this embodiment, some parts in the drawings will be omitted, enlarged or reduced, which do not represent the size of the actual product.

For those skilled in the art, it is understandable that some well-known structures and their descriptions may be omitted in the drawings.

The technical solution of the present invention will be further described below in combination with the accompanying drawings and embodiments.

Embodiment 1

Figure 4:
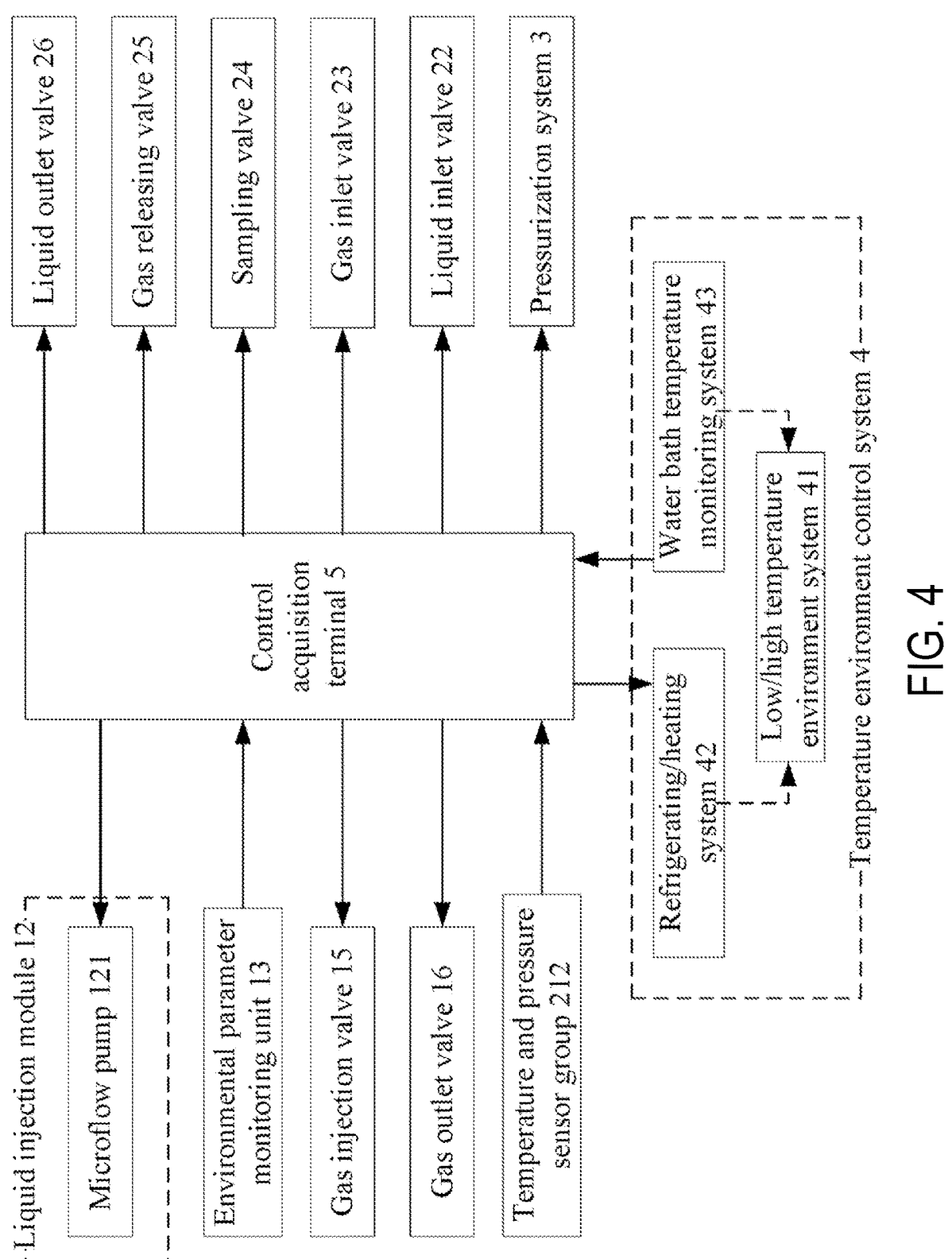
FIG. 4 is a schematic diagram of the circuit module connection of a control-acquisition terminal according to the present invention.

As shown in FIG. 1 and FIG. 4, the present embodiment proposes a high-pressure environment biological enrichment and spray-type solid isolation and cultivation device, including a spray-type isolation and cultivation solid unit 1, a biological enrichment unit 2, a pressurization system 3, a temperature environment control system 4 and a control-acquisition terminal 5. In particular, the biological enrichment unit 2 is used to realize enrichment and multi-stage purification process of marine microorganisms, obtain a biological enrichment fluid and inject the biological enrichment fluid into the spray-type isolation and cultivation solid unit 1. The spray-type isolation and cultivation solid unit 1 is use to convert the biological enrichment fluid into a state of microbeads, so that the biological enrichment fluid can be isolated and cultivated in a dispersed state, and culturability of the marine microorganisms is effectively improved. The pressurization system 3 and the temperature environment control system 4 are both connected to the spray-type isolation and cultivation solid unit 1 and the biological enrichment unit 2, for constructing a high-pressure, low-temperature environment consistent with the marine environment within the biological enrichment unit 2 and the spray-type isolation and cultivation solid unit 1, ensuring that enriched deep-sea microorganisms are enriched, purified, isolated and cultivated under in-situ environmental conditions. A control terminal and a signal detection terminal of the spray-type isolation and cultivation solid unit 1 and a control terminal and a signal detection terminal of the biological enrichment unit 2 are electrically connected to the control-acquisition terminal 5.

In the specific implementation process, the control-acquisition terminal 5 includes a data acquisition device, a data central processing unit and an operating computer and the like to realize the monitoring of various environmental data information changes during the enrichment, isolation and purification of microbial enrichment bacteria in a high-pressure environment, and functions such as real-time acquisition, processing, storage and image output.

Figure 2:
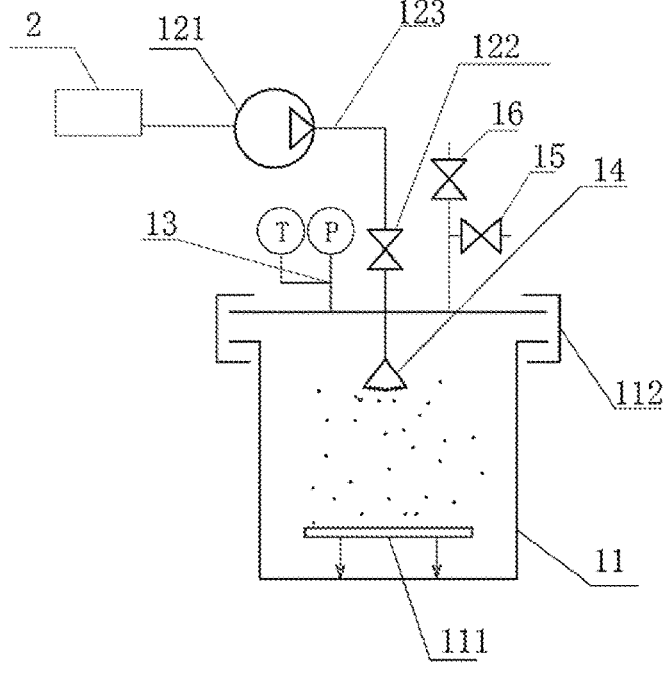
FIG. 2 is a schematic structural diagram of a spray-type isolation and cultivation chamber according to the present invention.

More specifically, as shown in FIG. 2 and FIG. 4, the spray-type isolation and cultivation solid unit 1 includes a spray-type isolation and cultivation chamber 11, a liquid injection module 12, an environmental parameter monitoring unit 13, a microporous nozzle 14, a gas injection valve 15 and a gas outlet valve 16. In particular, the spray-type isolation and cultivation chamber 11 is internally provided with solid culture plate 111, for isolating and culturing the microorganisms. The spray-type isolation and cultivation chamber 11 is placed in the temperature environment control system 4, and the temperature environment control system 4 ensures that a temperature in the spray-type isolation and cultivation chamber 11 is kept constant and consistent with a submarine temperature of a deep-sea cold spring area. The environmental parameter monitoring unit 13 is used to monitor temperature and pressure changes inside the spray-type isolation and cultivation chamber 11, and transmit data to the control-acquisition terminal 5. The microporous nozzle 14 is disposed inside the spray-type isolation and cultivation chamber 11, and is connected to the liquid injection module 12 disposed outside the spray-type isolation and cultivation chamber 11. An input end of the liquid injection module 12 is connected to a liquid output end of the biological enrichment unit 2, for injecting the biological enrichment fluid into the spray-type isolation and cultivation chamber 11, after passing through the microporous nozzle 14, the biological enrichment fluid will be dispersed into the state of microbeads scattered on the solid culture plate 111. The gas injection valve 15 and the gas outlet valve 16 are both disposed on the spray-type isolation and cultivation chamber 11, and the gas injection valve 15 is connected to the pressurization system 3, for injecting a gas into the spray-type isolation and cultivation chamber 11 to increase an internal pressure thereof. A control terminal of the gas outlet valve 16 is electronically connected to the control-acquisition terminal 5, for controlling the gas to be discharged from the spray-type isolation and cultivation chamber 11 to reduce the internal pressure thereof.

More specifically, the liquid injection module 12 includes a microflow pump 121, a liquid injection port 122 and a liquid delivery pipeline 123. In particular, an input end of the microflow pump 121 is connected to the liquid output end of the biological enrichment unit 2, and an output end of the microflow pump 121 is connected to the liquid injection port 122 by the liquid delivery pipeline 123. The liquid injection port 122 is connected to the microporous nozzle 14.

More specifically, the spray-type isolation and cultivation chamber 11 is provided with a quick-opening clamp 112.

In the specific implementation process, the spray-type isolation and cultivation chamber 11 involved in the present embodiment utilizes the principle of spray-type isolation to inject a microbial enrichment cultivation solution of the biological enrichment unit 2 into the spray-type isolation and cultivation chamber 11 through the microflow pump 121, via the microporous nozzle 14, the microbial enrichment cultivation solution is dispersed into an ultramicro strain, scattering on a solid medium, and after a single tiny droplet that is small enough is attached on the solid medium, the process of isolation and cultivation will be realized. The spray-type isolation and cultivation chamber 11 involved in the present solution is provided with a liquid injection port 122, which is used to inject a microbial enrichment bacteria solution into the spray-type isolation and cultivation chamber 11. The spray-type isolation and cultivation chamber 11 is further provided with a gas injection valve 15, which is used to inject a gas needed for growth of the microorganisms or an inert gas into the spray-type isolation and cultivation chamber 11 to pressurize the cultivation chamber. A high-strength solid culture plate 111 is placed inside the spray-type isolation and cultivation chamber 11, which is used to fill the solid medium to meet the needs of the implantation and growth of the microorganisms. Inside the spray-type isolation and cultivation chamber 11, it is provided with a key component to disperse the bacteria solution: the microporous nozzle 14, which can be spherical, trumpet-shaped or lotus-shaped, etc., so that the microbial enrichment bacteria solution can be dispersed into uniform fine droplets in a high-pressure environment after coming out of the liquid injection port 122. The pore size on the nozzle is fine enough and sufficient, so that the bacteria solution can be isolated and grown after being sprayed. The distance between the microporous nozzle 14 and the solid culture plate 111 should be such that the sprayed bacteria solution just adheres to the solid culture plate 111 evenly, and will not be scattered on an inner wall of the spray-type isolation and cultivation chamber 11.

Figure 3:
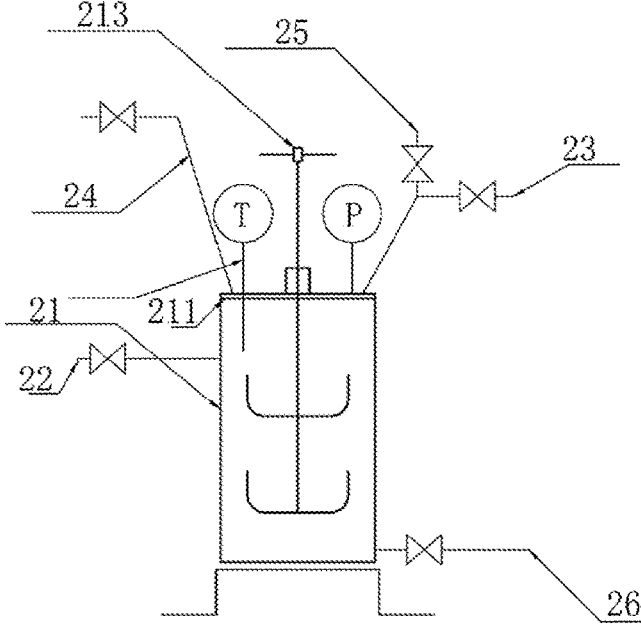
FIG. 3 is a schematic structural diagram of a high-pressure microbial enrichment cultivation kettle according to the present invention.

More specifically, as shown in FIG. 3 and FIG. 4, the biological enrichment unit 2 consists of a plurality of high-pressure microbial enrichment cultivation kettles 21 connected in series. A removable sealing lid 211 and a connecting sampling valve group are provided on the high-pressure microbial enrichment cultivation kettle 21, which is internally provided with a temperature and pressure sensor group 212. Each of the high-pressure microbial enrichment cultivation kettles 21 is disposed in the temperature environment control system 4. In particular, the removable sealing lid 211 is used to facilitate the sterilization operation inside the high-pressure microbial enrichment cultivation kettle 21 and put into the cultivation substrate. The connecting sampling valve group is used for connection and sampling of each of the high-pressure microbial enrichment cultivation kettles 21, the connecting sampling valve group is connected to the pressurization system 3, for feeding a liquid or a gas into the high-pressure microbial enrichment cultivation kettle 21 to increase a pressure in the high-pressure microbial enrichment cultivation kettle 21, making a pressure value in the high-pressure microbial enrichment cultivation kettle 21 consistent with an actual situation in a deep sea. The temperature and pressure sensor group 212 is used to monitor temperature and pressure changes in the high-pressure microbial enrichment cultivation kettle 21 in real time, and send a signal to the control-acquisition terminal 5.

More specifically, a stirring rod 213 is provided on the high-pressure microbial enrichment cultivation kettle 21. The stirring rod 213 is used for the high-pressure microbial enrichment cultivation kettle 21 to enhance a reaction process of a substrate during a cultivation process.

In the specific implementation process, the high-pressure microbial enrichment cultivation kettle 21 is designed with the stirring rod 213 on the top, which can enhance mass transfer by manual or mechanical stirring, enhance the reaction process of the substrate during the cultivation process, and increase the energy and nutrient utilization efficiency of the microorganisms.

More specifically, the connecting sampling valve group includes a liquid inlet valve 22, a gas inlet valve 23, a sampling valve 24, a gas releasing valve 25 and a liquid outlet valve 26. In particular, the high-pressure microbial enrichment cultivation kettles 21 are connected in series through the liquid outlet valve 26 and the liquid inlet valve 22, the liquid outlet valve 26 of the former high-pressure microbial enrichment cultivation kettle 21 is connected to the liquid inlet valve 22 of the latter high-pressure microbial enrichment cultivation kettle 21. The gas inlet valve 23 is used to input gas into the high-pressure microbial enrichment cultivation kettle 21 to increase the pressure in the high-pressure microbial enrichment cultivation kettle 21, making the pressure value in the high-pressure microbial enrichment cultivation kettle 21 consistent with the actual situation in the deep sea. The gas releasing valve 25 is used to release the gas in the high-pressure microbial enrichment cultivation kettle 21 to reduce the pressure in the high-pressure microbial enrichment cultivation kettle 21, and a control terminal thereof is electrically connected to the control-acquisition terminal 5. The sampling valve 24 is used to conduct real-time sampling analysis of the microorganisms in the high-pressure microbial enrichment cultivation kettle 21.

In the specific implementation process, the high-pressure microbial enrichment cultivation kettle 21 is provided with the sampling valve 24, which is used to analyze and detect samples during the enrichment process, so as to adjust the corresponding environmental parameters and optimize the enrichment cultivation process.

In the specific implementation process, the plurality of the high-pressure microbial enrichment cultivation kettles 21 consist the biological enrichment unit 2, the bacteria solution in the former high-pressure microbial enrichment cultivation kettle 21 is transferred to the latter high-pressure microbial enrichment cultivation kettle 21 by holding pressure, and so on, the bacteria solution is diluted according to the concentration gradient, the microbial bacteria solution obtained in the final-stage high-pressure microbial enrichment cultivation kettle 21 will supply the enriched and highly purified functional microorganisms under the stress of the nutrient conditions under the high-pressure environment. The pressure-holding transfer can be realized by taking out the enrichment liquid in the former high-pressure microbial enrichment cultivation kettle 21 through the sampling valve and pumping it into the latter high-pressure microbial enrichment cultivation kettle 21 through the micro-injection pump 24. The pressure of the latter high-pressure microbial enrichment cultivation kettle 21 may also be pressurized to slightly less than the previous high-pressure microbial enrichment cultivation kettle 21, and then the liquid outlet valve 26 of the previous high-pressure microbial enrichment cultivation kettle 21 and the liquid inlet valve 22 of the latter high-pressure microbial enrichment cultivation kettle 21 can be opened, the microbial enrichment fluid will automatically enter into the later high-pressure microbial enrichment cultivation kettle 21 from the later high-pressure microbial enrichment cultivation kettle 21 for purification and cultivation under the condition of slight pressure difference. During the whole process of multi-enrichment and liquid isolation and purification cultivation, the temperature and pressure environmental conditions of the high-pressure microbial enrichment cultivation kettle 21 are consistent with the environmental conditions of the microorganisms in the deep sea, ensuring the effectiveness of enrichment cultivation.

More specifically, the temperature environment control system 4 includes a low/high temperature environment system 41, a refrigerating/heating system 42 and a water bath temperature monitoring system 43. The spray-type isolation and cultivation solid unit 1 and the biological enrichment unit 2 are both disposed in the low/high temperature environment system 41 for a water bath, and the low/high temperature environment system 41 is connected to the refrigerating/heating system 42 to realize heat exchange. The water bath temperature monitoring system 43 is used to monitor temperature and pressure changes in the low/high temperature environment system 41, and transmit monitoring data to the control-acquisition terminal 5. A control terminal of the refrigerating/heating system 42 is electrically connected to the control-acquisition terminal 5.

In the specific implementation process, the maintenance of the constant temperature conditions of the spray-type isolation and cultivation chamber 11 and the high-pressure microbial enrichment cultivation kettle 21 is mainly to place the spray-type isolation and cultivation chamber 11 and the high-pressure microbial enrichment cultivation kettle 21 in the low/high temperature environment system 41 monitoring the temperature for the water bath, and through the heat exchange with the low/high temperature environmental system 41, the constant temperature state in the spray-type isolation and cultivation chamber 11 and the high-pressure microbial enrichment cultivation kettle 21 is maintained. Or the spray-type isolation and cultivation chamber 11 and the high-pressure microbial enrichment cultivation kettle 21 are placed in an air heat exchange constant temperature room.

In the specific implementation process, the temperature conditions in the spray-type isolation and cultivation chamber 11 and high-pressure microbial enrichment cultivation kettle 21 involved in the above solution are mainly controlled by the low/high temperature environment system 41. For example, a ring-wall cavity of the spray-type isolation and cultivation chamber 11 and a ring-wall cavity of the high-pressure microbial enrichment cultivation kettle 21 are injected with a cold/hot fluid, by circulating cooling or heating the fluid, the low temperature or high temperature state of the fluid in the ring-wall cavity is ensured, and then by the heat exchange between the cold/hot fluid and the built-in cavity, the low temperature or high temperature state in the built-in cavity is ensured. Or the spray-type isolation and cultivation chamber 11 and the high-pressure microbial enrichment cultivation kettle 21 are placed in a low temperature/high temperature water bath/oil bath environment, special temperature conditions required in the spray-type isolation and cultivation chamber 11 and the high-pressure microbial enrichment cultivation kettle 21 are ensured. Or the spray-type isolation and cultivation chamber 11 and the high-pressure microbial enrichment cultivation kettle 21 are placed in a cooling/heating room or box with a constant temperature guaranteed by air heat exchange. Some extreme temperature conditions can be maintained by using several temperature control methods mentioned above at the same time. It monitors the temperature in real time through the environmental parameter monitoring unit 13 and the temperature and pressure sensor group 212.

More specifically, as shown in FIG. 1 and FIG. 4, the pressurization system 3 includes an air compressor 31, a booster pump 32, a gas storage tank 33, a pressure regulating valve 34 and a ventilation pipeline 35. In particular, the air compressor 31, the booster pump 32, the gas storage tank 33 and the pressure regulating valve 34 are connected in sequence through the ventilation pipeline 35, and finally are connected to the spray-type isolation and cultivation solid unit 1 and the biological enrichment unit 2 in sequence through the ventilation pipeline 35, for injecting a gas into the spray-type isolation and cultivation solid unit 1 and the biological enrichment unit 2 for pressurization. The pressure regulating valve 34 is used to regulate an internal pressure of the spray-type isolation and cultivation solid unit 1 and the biological enrichment unit 2. A control terminal of the air compressor 31, a control terminal of the booster pump 32 and a control terminal of the pressure regulating valve 34 are all electrically connected to the control-acquisition terminal 5.

In the specific implementation process, the pressurization system 3 involved in the present embodiment is mainly used to inject the gas into the high-pressure microbial enrichment cultivation kettle 21 and the spray-type isolation and cultivation chamber 11 for pressurization, so that pressure environment in the high-pressure microbial enrichment cultivation kettle 21 and the spray-type isolation and cultivation chamber 11 is consistent with the pressure value of the microorganisms in the ocean in-situ.

In the specific implementation process, the pressure changes in the cultivation chamber are monitored in real time through the environmental parameter monitoring unit 13 and the temperature and pressure sensor group 212, and by the pressurization and decompression of the cultivation chamber carried out through active inflation/deflation, the pressure value in the cultivation chamber is kept consistent with the marine environmental conditions for the growth of the microorganisms.

More specifically, the high-pressure environment biological enrichment and the spray-type solid isolation and cultivation device further include a movable platform 6, and the spray-type isolation and cultivation solid unit t 1, the biological enrichment unit 2, the pressurization system 3, the temperature environment control system 4 and the control-acquisition terminal 5 are all disposed on the movable platform, for increasing universality of cultivation scenarios.

In the specific implementation process, the biological enrichment unit 2 can realize the enrichment cultivation of microorganisms under the temperature and pressure environment conditions of the ocean in-situ, and the spray-type isolation and cultivation solid unit 1 can convert the biological enrichment fluid into the state of microbeads, so that the biological enrichment fluid can be isolated and cultivated in a dispersed state. By reshaping its in-situ environment to carry out enrichment cultivation and isolation of marine microorganisms, the problem of isolation and pure cultivation of the marine microorganisms in high-pressure environment is solved, the cultivability of the marine microorganisms is improved, a pure cultivation technology is formed, and an important basic means is provided for the development and utilization of high-pressure environment microbial resources.

Embodiment 2

Figure 5:
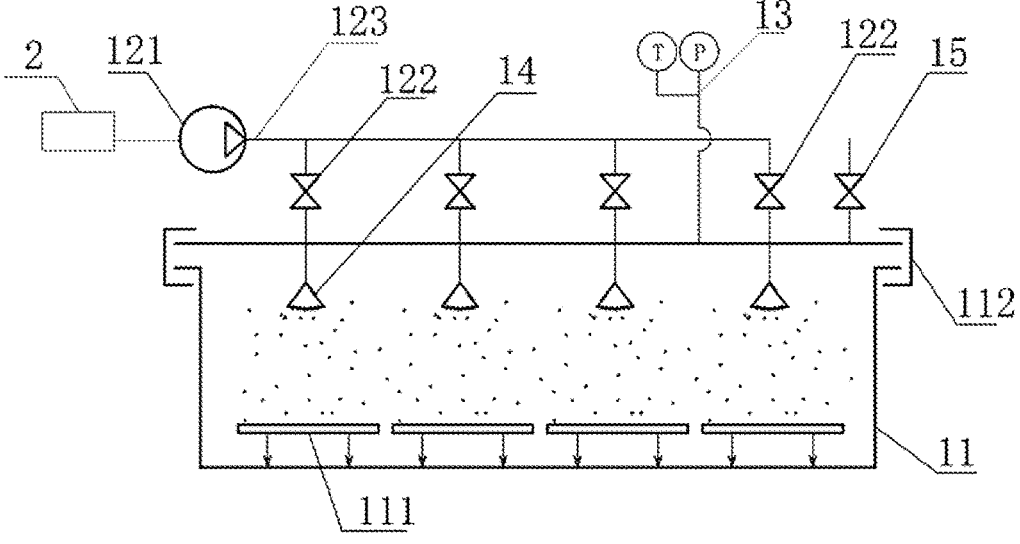
FIG. 5 is a schematic structural diagram of the spray-type isolation and cultivation solid unit according to an embodiment of the present invention to realize lateral isolation and cultivation of microorganisms under the same temperature and pressure conditions.

More specifically, on the basis of the Embodiment 1, as shown in FIG. 5, the spray-type isolation and cultivation solid unit 1 is provided with a plurality of the microporous nozzles 14 and a plurality of the solid culture plates 111. The liquid injection module 12 is connected to each of the microporous nozzles 14 simultaneously. The solid culture plates 111 are disposed laterally at a bottom of the spray-type isolation and cultivation solid unit 1 to realize lateral isolation and cultivation of the microorganisms under conditions of the same temperature and same pressure.

Figure 6:
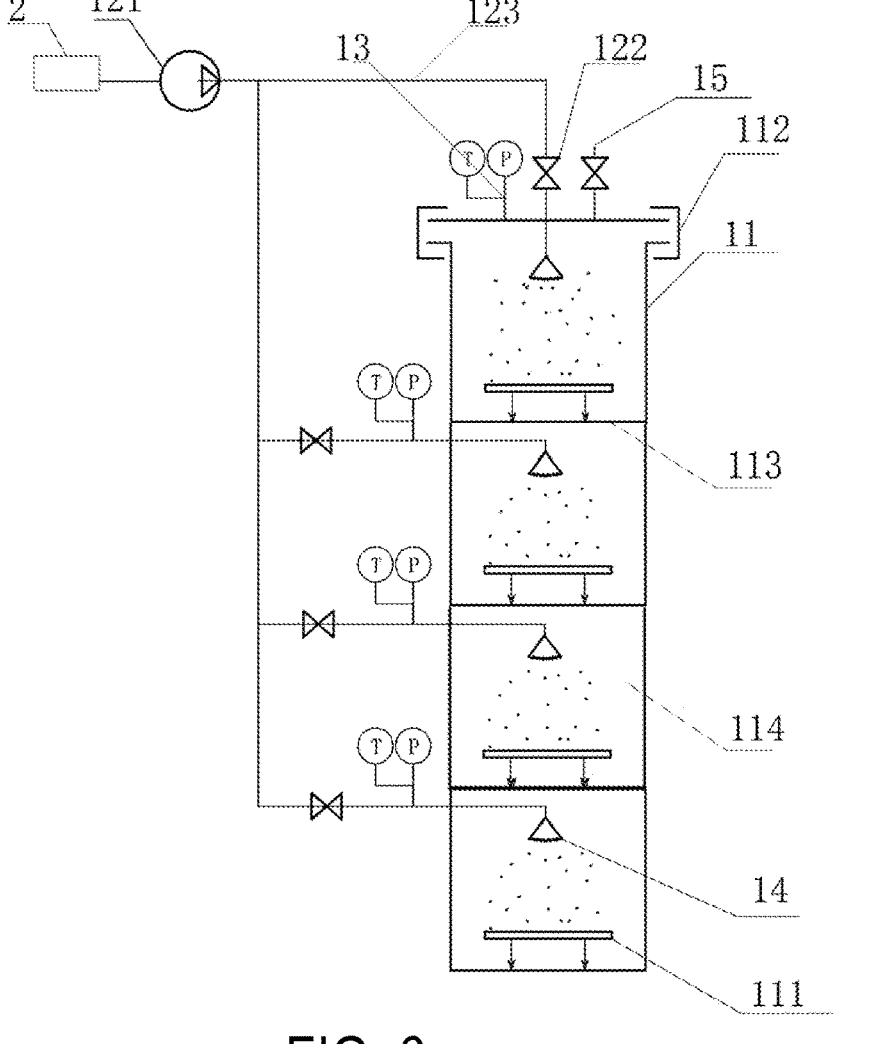
FIG. 6 is a schematic structural diagram of the spray-type isolation and cultivation solid unit according to an embodiment of the present invention to realize vertical isolation and cultivation of microorganisms under the same temperature and pressure conditions.

More specifically, on the basis of the Embodiment 1, as shown in FIG. 6, the spray-type isolation and cultivation chamber 11 is provided with a plurality of connecting partitions 113 in a vertical direction, partitioning the spray-type isolation and cultivation chamber 11 into a plurality of connecting cultivation cavities 114. In particular, a solid culture plate 111 is provided on each of the connecting partitions 113, and the microporous nozzle 14 is provided inside each of the cultivation cavities 114. The liquid injection module 12 is connected to each of the microporous nozzles 14 simultaneously, realizing vertical isolation and cultivation of the microorganisms under conditions of the same temperature and same pressure.

More specifically, on the basis of the Embodiment 1, the spray-type isolation and cultivation solid unit 1 includes a plurality of the spray-type isolation and cultivation chambers 11, each of the spray-type isolation and cultivation chambers 11 is provided with an independent microporous nozzle 14, an independent solid culture plate 111 and an independent gas injection valve 15. All of the spray-type isolation and cultivation chambers 11 are placed in the same temperature environment control system 4. The liquid injection module 12 is connected to the microporous nozzle 14 in each of the spray-type isolation and cultivation chambers 11 simultaneously, realizing isolation and cultivation of the microorganisms under conditions of the same temperature and different pressures.

More specifically, on the basis of the Embodiment 1, the spray-type isolation and cultivation solid unit 1 includes a plurality of the spray-type isolation and cultivation chambers 11, and each of the spray-type isolation and cultivation chambers 11 is provided with an independent microporous nozzle 14, an independent solid culture plate 111 and an independent gas injection valve 15. Each of the spray-type isolation and cultivation chamber 11 is placed in an independent temperature environment control system 4 which is correspondingly provided. The liquid injection module 12 is connected to the microporous nozzle 14 in each of the spray-type isolation and cultivation chamber 11 simultaneously, and all of the gas injection valves 15 are in communication, realizing isolation and cultivation of the microorganisms under conditions of different temperatures and same pressure.

In the specific implementation process, by cutting off the communication between all the gas injection valves 15 and controlling them separately, isolation and cultivation of the microorganisms under conditions of different temperatures and different pressures can be realized.

In order to improve the screening efficiency of the microorganisms, the isolation process of the microorganisms in the high-pressure environment involved in the present embodiment uses the single spray-type isolation and cultivation chamber 11 for multi-stage combined cultivation to form a cultivation process. Under the same temperature and pressure environmental conditions, in order to increase the cultivation area and the sorting volume, a plurality of solid culture plates 111 can be arranged in the lateral cultivation chamber, each solid culture plate 111 can be filled with medium with different nutrients, and each plate is provided with one microporous nozzle 14 to improve the efficiency of isolation and cultivation. It can also be arranged as a tower structure, where the plurality of solid culture plates 111 are combined with the microporous nozzles 14 for vertical stacking, or multiple groups can be combined horizontally and vertically for large-scale cultivation. The entire spray-type isolation and cultivation chamber 11 is set to the same temperature and pressure environmental conditions. If in order to screen strains under different environment conditions of pressure and temperature, different spray-type isolation and cultivation chambers 11 can also be combined in parallel, the temperature and pressure environment of each spray-type isolation and cultivation chamber 11 can be controlled separately, and the temperature and pressure parameters can be set gradiently according to the sorting purpose. The plurality of the spray-type isolation and cultivation chambers are combined in parallel and connected to the microflow pump 121 and the final-stage high-pressure microbial enrichment cultivation kettle 21. The sorting process is formed under different temperature and pressure environmental conditions.

Figure 7:
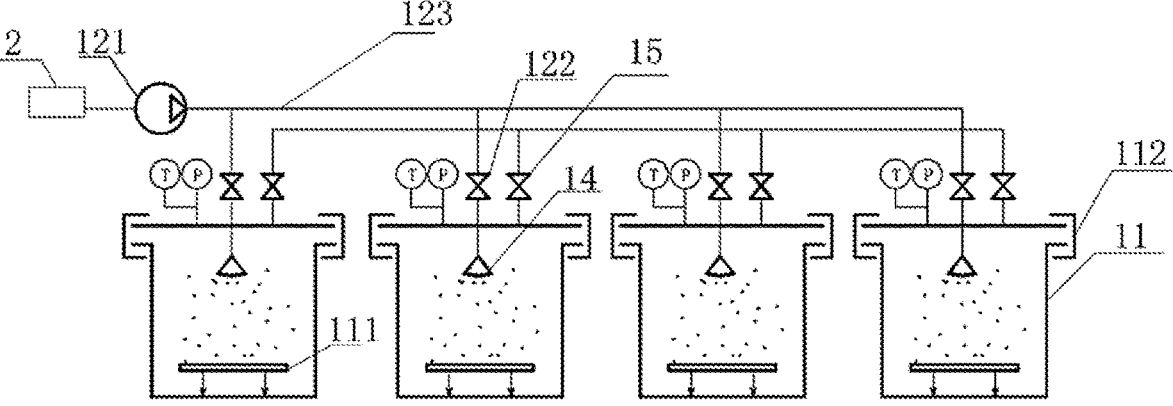
FIG. 7 is a schematic structural diagram of the spray-type isolation and cultivation solid unit according to an embodiment of the present invention to realize the cultivation of microorganisms in different mediums under the same temperature and pressure conditions.

The present embodiment improves the cultivability of microorganisms by constructing a high-pressure environment for microorganisms in a high-pressure microorganism enrichment cultivation kettle 21 and a spray-type isolation and cultivation chamber 11 for microorganisms in a high-pressure environment, such as the high pressure and extreme temperature environmental conditions of life in the marine environment. Through multi-stage enrichment and liquid dilution cultivation, functional microorganisms with high purity under directional environmental stress are obtained, and at the same time, combined with spray-type solid cultivation isolation, monoclonal microorganisms colonies are obtained. The whole process of enrichment and isolation is carried out under the in-situ pressure and temperature environment of the microorganisms. At the same time, multiple sets of isolation and cultivation chambers can be combined to form an efficient isolation process with different medium combinations. As shown in FIG. 7, the microorganisms are cultivated in different medium under the same temperature and pressure conditions.

Embodiment 3

The high-pressure environment marine microbial enrichment cultivation and isolation technology involved in the present embodiment mainly includes two steps of enrichment and isolation. First, through enrichment cultivation of the biological enrichment unit 2, after obtaining the microflora with higher purity, the microflora enter the spray-type isolation and cultivation chamber 11 under the condition of maintaining pressure for solid cultivation and isolation, and through simultaneously screening the combined process of different cultivation medium and environmental conditions, a pure cultivation strain is obtained. Specifically:

Enrichment Cultivation Process:

The first is to sterilize the high-pressure microbial enrichment cultivation kettle 21 and its accompanying pipes and valves, the substrates to be cultivated, such as deep-sea sediments, macrobiological tissues and extracts symbiotic with microorganisms, are then loaded in sequence, the nutrient solution required for cultivation is then loaded from the liquid inlet valve 22, and then the gas required for the cultivation (if it is not required, inert gas can be injected) is injected from the gas inlet valve 23 to increase the pressure value in the high-pressure microorganism enrichment cultivation kettle 21 to be consistent with the actual environmental conditions in the deep sea. During the cultivation process, the stirring rod 213 on the top is used to increase the mass transfer effect and optimize the cultivation process. After the first-stage high-pressure microbial enrichment cultivation kettle 21 has completed the cultivation process, nutrient solution needed for cultivation is injected into the second-stage high-pressure microbial enrichment cultivation kettle 21, and gas and the nutrient solution are injected into the second-stage high-pressure microbial enrichment cultivation kettle 21 by the pressurization system 3 for pressurization, the amount of the cultivation solution injected into the second-stage high-pressure microbial enrichment cultivation kettle 21 needs to be based on the sorting requirements to ensure a dilution ratio of the concentration of the enrichment from the first-stage high-pressure microbial enrichment cultivation kettle 21 into the second-stage high-pressure microbial enrichment cultivation kettle 21, and then the microbial bacteria solution in the first-stage high-pressure microbial enrichment cultivation kettle 21 is transferred to the second-stage high-pressure microbial enrichment cultivation kettle 21 through pressure-holding transfer. By that analogy, the microorganisms in the final-stage high-pressure microbial enrichment cultivation kettle 21 will reach a highly purified state. When the concentration of deep-sea microbial bacteria solution in the final-stage high-pressure microbial enrichment cultivation kettle 21 reaches more than 106 per mL, it can be considered that a better purification state has been achieved. For specific cultivated microorganisms, the dilution ratio of each stage can be adjusted.

When the concentration of the bacterial solution in the enrichment cultivation process has been identified to meet the requirements, it will enter into the solid isolation and cultivation process.

Solid Isolation and Cultivation Process:

The first is to sterilize the spray-type isolation and cultivation chamber 11 and all its internal devices and related pipes and valves to keep them sterile. Then the plate is filled with the sterilized solid medium. In order to avoid the solid agar medium from liquefying or forming a porous structure under high pressure conditions, the solid culture plate 111 can be filled with alumina powder, fine glass beads/steel balls, steel wire balls, etc. as a support to meet the needs of solid isolation and cultivation. Then the temperature environment control system 4 is turned on to ensure that the temperature in the spray-type isolation and cultivation chamber 11 is consistent with the temperature conditions of the microorganisms in the marine environment. Then gas is injected into the spray-type isolation and cultivation chamber 11 through the gas injection valve 15 for pressurization, so that the pressure conditions in the spray-type isolation and cultivation chamber 11 are consistent with the pressure conditions of the microorganisms living in the marine environment. After ensuring that all system components are working properly, the microflow pump 121 is turned on and the microbial enrichment fluid is injected into the spray-type isolation and cultivation chamber 11 from the final-stage high-pressure microbial enrichment cultivation kettle 21, after the microbial enrichment fluid passes through the microporous nozzle 14, it will be divided into ultra-fine uniform droplets, and the ultra-fine droplets will be transported to the solid culture plate 111 at the bottom of the spray-type isolation and cultivation chamber 11 under the action of gravity. The ultra-fine droplets are implanted and grown in the solid medium, and after a sufficient incubation period, isolated single colonies will grow.

The automatic cultivation process of microorganisms involved in the present embodiment mainly includes two conditions, the same temperature and pressure conditions and different temperature and pressure conditions. The same temperature and pressure conditions are mainly to meet the needs of large-scale simultaneous screening and isolation of different medium. First, in the spray-type isolation and cultivation chamber 11, several solid culture plates 111 and microporous nozzles 14 are placed in combination horizontally or vertically, all the inlets of the microporous nozzles 14 are connected in parallel by pipeline and to the micro-injection pump and the final-stage high-pressure microbial enrichment cultivation kettle 21. Different temperature and pressure conditions are mainly to combine different spray-type isolation and cultivation chambers 11 in parallel, the temperature and pressure environment of each spray-type isolation and cultivation chamber 11 are individually controlled, and the parameter conditions can be set in a gradient according to the sorting purpose. The plurality of the spray-type isolation and cultivation chambers 11 are combined in parallel and connected to the microflow pump 121 and the final-stage high-pressure microorganism enrichment cultivation kettle 21. When the whole process is assembled and debugged, all the cultivation chamber 11 and the pipes and the valves involved in the cultivation process are sterilized as a whole. Then through temperature and pressure monitoring, it is ensured that the temperature and pressure environmental conditions in all spray-type isolation and cultivation chambers are consistent with the temperature and pressure environmental conditions of the marine environment where the microorganisms are located. The micro-injection pump is turned on, and the finely dispersed droplets will be implanted on the solid culture plate 111 for isolation and cultivation, which can realize the automatic sorting process under different medium environments, and effectively ensure the isolation, cultivation and purification of the microorganisms in the high-pressure environment. Key technologies are provided for efficient utilization and sorting process of microorganisms in high-pressure environment.

The present embodiment mainly relates to the continuous enrichment, spray-type isolation and cultivation device and process of microorganisms under high-pressure environment, and proposes a cultivation device and technical method for multi-stage enrichment cultivation and multi-medium spray-type automatic isolation and purification of marine microorganisms under high pressure and extreme temperature environmental conditions.

The present embodiment solves the problem that the existing indoor pure cultivation technology method is separated from the high pressure and extreme temperature environmental conditions for the survival of microorganisms, which leads to the poor survival activity of a large number of microorganisms and cannot achieve pure cultivation. This solution does not require professional operators, and can be used in multi-cultivation scenarios such as research laboratories and scientific research ships, and has wide adaptability.

The present embodiment does not require manual enrichment and streak isolation operations by professionals, and can be enriched and sorted on a large scale, reducing labor costs, and realizing automated isolation and cultivation of high-pressure environment microorganisms under in-situ pressure and temperature environmental conditions. Under the high-pressure environment, pure cultivation of microorganisms in-situ provides an important technical means.

Compared with the existing pure cultivation technology, this solution proposes a high-pressure pure cultivation technology for enrichment and isolation and cultivation of microorganisms in extreme environmental conditions under high-pressure environment conditions, and solves the problem that the existing atmospheric isolation and cultivation technology is separated from the temperature and pressure environmental conditions of high-pressure environment microorganisms in-situ survival, resulting in poor activity of most microorganisms, or the phenotype is greatly different from the in-situ environmental conditions, and cannot be isolated and cultivated. Compared with the existing isolation and cultivation technology, this solution can effectively reduce the investment of professionals, and can carry out large-scale enrichment and isolation and cultivation, improve the screening efficiency of difficult-to-cultivate microorganisms, and improve the screening and cultivation efficiency of functional bacteria in high-pressure environment.

Embodiment 4

In order to further illustrate the technical realization process and technical effect of this solution, the present embodiment proposes a multi-stage enrichment and isolation device for directional enrichment and isolation of deep-sea methanotrophs under high-pressure environment. The high-pressure microbial enrichment cultivation kettle 21 and the spray-type isolation and cultivation chamber 11 are the core of this example, other auxiliary systems include the pressurization system 3, the temperature environment control system 4 and the control-acquisition terminal 5. By constructing the high pressure and low temperature environmental conditions for methanotrophs in the deep-sea cold spring area to live in the deep sea environment in the high-pressure microorganism enrichment cultivation kettle 21 and the spray-type isolation and cultivation chamber 11 of the high-pressure environment microorganisms, their survival activity is improved. In this example, deep-sea methanotrophs with high purity under high pressure, low temperature, and methane as the sole carbon source were obtained through multi-stage enrichment and liquid dilution cultivation, and at the same time combined with spray-type solid cultivation and isolation, monoclonal microorganisms colonies were obtained. The whole process of enrichment and isolation was carried out under the conditions of in-situ pressure (14 MPa) and temperature environment (4° C.) in the hippocampus cold spring area in the South China Sea. At the same time, multiple sets of isolation and cultivation chambers can be combined to form an efficient isolation process with different medium combinations.

The successful enrichment of deep-sea methanotrophs within the biological enrichment unit, and the successful purification and isolation of the enriched bacteria solution on spray-type isolation and cultivation solid unit 1 are the keys to this example. The bottom of the enrichment cultivation and isolation and cultivation chamber is provided with the movable platform 6 to increase the universality of cultivation scenarios.

The biological enrichment unit involved in the present embodiment is mainly formed by connecting a plurality of the high-pressure microbial enrichment cultivation kettles 21 in series. The high-pressure microbial enrichment cultivation kettle 21 is designed with an openable lid, which is convenient to put into the cultivation substrate and sterilize. The top of the high-pressure microbial enrichment cultivation kettle 21 is designed with a stirring rod 213, which is used to enhance the reaction process of the substrate and increase the carbon source and energy utilization efficiency of deep-sea methanophiles during the cultivation. The high-pressure microbial enrichment cultivation kettle 21 is provided with a temperature and pressure sensor group 212, which monitors the temperature and pressure changes in the high-pressure microbial enrichment cultivation kettle 21 in real time. The maintenance of the constant temperature conditions of the high-pressure microbial enrichment cultivation kettle 21 is mainly to place the high-pressure microbial enrichment cultivation kettle 21 in a low temperature water bath of the low/high temperature environment system 41, and through the heat exchange with the water bath system and the low/high temperature environment system 41 is filled with refrigerants such as ethylene glycol, a low temperature in the enrichment cultivation room is maintained. The top of the high-pressure microbial enrichment cultivation kettle 21 is provided with a gas inlet valve 23 and a liquid inlet valve 22, through the gas inlet valve 23 and the liquid inlet valve 22, the methane gas and nutrient solution required for cultivation are injected to pressurize the closed high-pressure microbial enrichment cultivation kettle 21, realizing that the pressure value in the high-pressure microorganism enrichment cultivation kettle 21 is maintained at about 14 MPa. The high-pressure microbial enrichment cultivation kettle 21 is provided with a sampling valve 24, which is used to analyze and detect samples during the enrichment process, so as to adjust the corresponding environmental parameters and optimize the process of enrichment cultivation.

As shown in FIG. 1, in this example, the biological enrichment unit 2 consists of 4 high-pressure microbial enrichment cultivation kettles 21 connected in series, the bacteria solution in the high-pressure microbial enrichment cultivation kettle 21 is transferred to the latter high-pressure microbial enrichment cultivation kettle 2121 by holding pressure, and so on, the bacteria solution is diluted according to the concentration gradient, the microbial bacteria solution obtained in the final-stage high-pressure microbial enrichment cultivation kettle 21 will be highly purified deep-sea methanotrophs in a high-pressure environment. By pressurizing the pressure of the latter high-pressure microbial enrichment cultivation kettle 21 to 0.2-0.5 MPa lower than the pressure of the previous high-pressure microbial enrichment cultivation kettle 21, and then the sampling valve 24 of the previous high-pressure microbial enrichment cultivation kettle 21 and the liquid inlet valve 22 of the latter high-pressure microbial enrichment cultivation kettle 21 are opened, the microbial enrichment fluid will automatically enter the previous high-pressure microbial enrichment cultivation kettle 21 into the latter high-pressure microbial enrichment cultivation kettle 21 for purification and cultivation under the condition of a slight pressure difference. During the four multi-stage enrichment and purification processes, the temperature and pressure environment in the high-pressure microbial enrichment cultivation kettle 21 were kept at 4° C. and 14 MPa to ensure the effectiveness of enrichment cultivation.

The spray-type isolation and cultivation solid unit 1 involved in the present embodiment utilizes the principle of spray-type release, the solid culture plate 11 is placed inside the spray-type isolation and cultivation chamber 11, the methanotrophic enrichment cultivation solution in the final-stage high-pressure microbial enrichment cultivation kettle 21 is injected into the spray-type isolation and cultivation chamber 11 through the microflow pump 121, via the microporous nozzle 14, the methanotrophic enrichment cultivation solution is dispersed into an ultramicro strain, scattering on a solid medium, and after a single tiny droplet that is small enough is attached to the solid medium, the process of isolation and cultivation will be realized. The spray-type isolation and cultivation chamber 11 involved in the present embodiment is provided with a liquid injection port 122, which is used to inject the methanotrophic enrichment liquid into the solid cultivation chamber; and is further provided with a gas injection valve 15, which is used to inject the methane gas needed for the growth of methanotrophs into the spray-type isolation and cultivation chamber 11 to pressurize the cultivation chamber to 14 MPa. A high-strength solid culture plate 111 is placed inside the spray-type isolation and cultivation chamber 11, which is used to fill the solid medium to meet the needs of the implantation and growth of the methanotrophs. Inside the spray-type isolation and cultivation chamber 11, it is provided with a key component to disperse the bacteria solution: the trumpet-shaped microporous nozzle 14, which can disperse the methanotrophic enrichment liquid into uniform fine droplets after coming out of the liquid injection port 122. The pore size on the nozzle is fine enough and sufficient, so that the bacteria solution can be isolated and grown after being sprayed. The distance between the microporous nozzle 14 and the solid culture plate 111 is 100 mm, so that the bacteria solution sprayed out is just uniformly attached to the solid culture plate 111, rather than scattered on the inner wall of the spray-type isolation and cultivation chamber.

The pressurization system 3 involved in the present embodiment is mainly used to inject methane gas into the microbial enrichment and isolation and cultivation chamber for pressurization, so that the pressure environment in the spray-type isolation and cultivation chamber 11 and the high-pressure microbial enrichment cultivation kettle 21 can be maintained at 14 MPa.

The high-pressure environment deep-sea methanotrophic enrichment cultivation and isolation technology involved in the present embodiment mainly includes two steps of enrichment and isolation. First, through multi-stage high-pressure environment enrichment cultivation in the biological enrichment unit 2, after obtaining the deep-sea methanophiles with higher purity, the deep-sea methanophiles enter the spray-type isolation and cultivation chamber 11 under the condition of maintaining pressure for solid cultivation and isolation, and through simultaneously screening the combined process of different cultivation medium and environmental conditions, a pure cultivation strain is obtained.

The high-pressure environment deep-sea methanotrophic enrichment cultivation method involved in the present embodiment is firstly to sterilize the high-pressure microbial enrichment cultivation kettle 21 and its associated pipe valves, and then the high-pressure microbial enrichment cultivation kettle 21 is filled with the sediment in the methane leakage area of the hippocampus cold spring to be cultivated in sequence, and then the nutrient solution required for cultivation is loaded from the liquid inlet valve 22, and the methane required for the cultivation is injected from the gas inlet valve 23, so that the gas increases the pressure in the high-pressure microbial enrichment cultivation kettle 21 to 14 MPa. During the cultivation, stirring is performed by the stirring rod 213 on the top to increase mass transfer and optimize the cultivation process. After the enrichment cultivation process is completed, the nutrient solution needed for cultivation is injected into the second-stage high-pressure microbial enrichment cultivation kettle 21, and gas is injected into the second-stage high-pressure microbial enrichment cultivation kettle 21 through the pressurization system 3 for pressurization, the amount of the cultivation solution injected into the second-stage high-pressure microbial enrichment cultivation kettle 21 needs to ensure that the dilution ratio of the enrichment liquid from the concentration of the first-stage high-pressure microorganism enrichment and cultivation kettle 21 to the second-stage high-pressure microorganism enrichment and cultivation kettle 21 is 1:10, and then the microbial bacteria solution in the first-stage high-pressure microbial enrichment cultivation kettle 21 is transferred to the second-stage high-pressure microbial enrichment cultivation kettle 21 through pressure-holding transfer. By that analogy, the microorganisms in the final-stage high-pressure microbial enrichment cultivation kettle 21 will reach a highly purified state. When the concentration of deep-sea methanophilic bacteria solution in the final-stage high-pressure microbial enrichment cultivation kettle 21 reaches more than 106 per mL, it can be considered that a better purification state has been achieved. For specific cultivated microorganisms, the dilution ratio of each stage can be adjusted.

When the concentration of the bacterial solution in the enrichment process has been identified to meet the requirements, it will enter into the spray-type isolation and cultivation solid unit 1 for solid isolation and cultivation process. The isolation and cultivation process includes: the first is to sterilize the spray-type isolation and cultivation chamber 11 and all its internal devices and related pipes and valves to keep them sterile. Then the solid culture plate 111 is filled with the sterilized solid medium. In order to avoid the solid agar medium from liquefying or forming a porous structure under high pressure conditions, the solid culture plate 111 can be filled with fine glass beads as a support to meet the needs of solid isolation and cultivation. Then the temperature environment control system 4 is turned on to ensure that the temperature in the spray-type isolation and cultivation chamber 11 is consistent with the temperature conditions of methanotrophs in the hippocampus cold spring area. Then methane gas is injected into the spray-type isolation and cultivation chamber 11 through the gas injection valve 15 for pressurization, so that the pressure in the spray-type isolation and cultivation chamber 11 is increased to 14 MPa. After ensuring that all system components are working properly, the microflow pump 121 is turned on and the purified methanotrophic enrichment liquid is injected into the spray-type isolation and cultivation chamber 11 from the final-stage high-pressure microbial enrichment cultivation kettle 21, after the methanotrophic enrichment liquid passes through the microporous nozzle 14, it will be divided into ultra-fine uniform droplets, and the ultra-fine droplets will be transported to the solid culture plate 111 at the bottom of the spray-type isolation and cultivation chamber 11 under the action of gravity. The ultra-fine droplets are implanted and grown in the solid medium, and isolated single colonies will grow.

The automatic cultivation process of methanotrophs involved in the present embodiment mainly includes two conditions, the same temperature and pressure conditions and different temperature and pressure conditions. The same temperature and pressure conditions are mainly to meet the needs of large-scale simultaneous screening and isolation of different media. First, in the high spray-type isolation and cultivation chamber 11, several solid culture plates 111 and microporous nozzles 14 are placed in combination horizontally or vertically, all the inlets of the microporous nozzles 14 are connected in parallel by pipeline and to the micro-injection pump 121 and the final-stage high-pressure microbial enrichment cultivation kettle 21. During the whole process of screening, all solid culture plate 111 are under the environmental conditions of 14 MPa and 4° C. Different temperature and pressure conditions are mainly to combine different spray-type isolation and cultivation chambers 11 in parallel, the temperature and pressure environment of each high spray-type isolation and cultivation chamber 11 are individually controlled, and the parameter conditions can be set in a gradient according to the sorting purpose. For example, according to the methanotrophs found in different water depth environments, the pressure conditions in the plurality of the high spray-type isolation and cultivation chambers 11 are gradient facilities from 6 MPa to 20 MPa, and the temperature environment response is set to the submarine temperature of the depth environment. The plurality of the high spray-type isolation and cultivation chambers 11 are combined in parallel and connected to the microflow pump 121 and the final-stage high-pressure microorganism enrichment cultivation kettle 21. When the whole process is assembled and debugged, all the final-stage high-pressure microbial enrichment cultivation kettles 21 and the pipes and the valves involved in the cultivation process are sterilized as a whole. Then through temperature and pressure monitoring, it is ensured that the temperature and pressure environmental conditions in all final-stage high-pressure microbial enrichment cultivation kettle 21 are consistent with the temperature and pressure environmental conditions of the marine environment where the methanotrophs are located. The micro-injection pump 121 is turned on, and the finely dispersed droplets will be implanted on the solid culture plate 111 for isolation and cultivation, which can realize the automatic sorting process under different medium environments, and effectively ensure the isolation, cultivation and purification of the methanotrophs in the high-pressure environment. Key technologies are provided for efficient utilization and sorting process in high-pressure environment of deep-sea methanotrophs.

Obviously, the above-mentioned embodiments of the present invention are only examples for clearly illustrating the present invention, rather than limiting the implementation of the present invention. For those of ordinary skill in the art, on the basis of the above description, it is also possible to do make variation or changes in other forms. It is not necessary and impossible to list all the embodiments here. Any modifications, equivalent replacements and improvements made within the spirit and principle of the present invention should be included within the scope of protection claimed by the present invention.

What is claimed is:

1. A high-pressure environment biological enrichment and solid isolation and cultivation device, wherein the device comprises an isolation and cultivation solid unit, a biological enrichment unit, a pressurization system, a temperature environment control system and a control-acquisition terminal; wherein:

the biological enrichment unit is used to realize enrichment and multi-stage purification process of marine microorganisms, obtain a biological enrichment fluid and inject the biological enrichment fluid into the isolation and cultivation solid unit;

the isolation and cultivation solid unit is used to convert the biological enrichment fluid into a state of micro-beads, so that the biological enrichment fluid can be isolated and cultivated in a dispersed state, and culturability of the marine microorganisms is effectively improved;

the pressurization system and the temperature environment control system are both connected to the isolation and cultivation solid unit and the biological enrichment unit respectively, for constructing a high-pressure, low-temperature environment consistent with the marine environment within the biological enrichment unit and the isolation and cultivation solid unit, ensuring that enriched deep-sea microorganisms are enriched, purified, isolated and cultivated under in-situ environmental conditions, wherein the high-pressure is 6 MPa to 20 MPa; and both a control terminal and a signal detection terminal of the isolation and cultivation solid unit and a control terminal and a signal detection terminal of the biological enrichment unit are electrically connected to the control-acquisition terminal;

wherein the isolation and cultivation solid unit comprises an isolation and cultivation chamber, a liquid injection module, a microporous nozzle, a gas injection valve and a gas outlet valve; wherein:

the isolation and cultivation chamber is internally provided with a solid culture plate, for isolating and culturing the microorganisms;

the isolation and cultivation chamber is placed in the temperature environment control system, and the temperature environment control system ensures that a temperature in the isolation and cultivation chamber is kept constant and consistent with a submarine temperature of a deep-sea cold spring area;

the microporous nozzle is disposed inside the isolation and cultivation chamber, and is connected to the liquid injection module disposed outside the isolation and cultivation chamber; an input end of the liquid injection module is connected to a liquid output end of the biological enrichment unit, for injecting the biological enrichment fluid into the isolation and cultivation chamber, after passing through the microporous nozzle, the biological enrichment fluid will be dispersed into the state of microbeads scattered on the solid culture plate; and the gas injection valve and the gas outlet valve are both disposed on the isolation and cultivation chamber, and the gas injection valve is connected to the pressurization system, for injecting a gas into the isolation and cultivation chamber to increase an internal pressure thereof; and a control terminal of the gas outlet valve is electrically connected to the control-acquisition terminal, for controlling the gas to be discharged from the isolation and cultivation chamber to reduce the internal pressure thereof;

the biological enrichment unit consists of a plurality of high-pressure microbial enrichment cultivation kettles connected in series; a removable sealing lid and a connecting sampling valve group are provided on the high-pressure microbial enrichment cultivation kettles which is internally provided with a temperature and pressure sensor group; and each of the high-pressure microbial enrichment cultivation kettles is disposed in the temperature environment control system; wherein:

the removable sealing lid is used to facilitate sterilization of an interior of the high-pressure microbial enrichment cultivation kettles and placement of a cultivation substrate;

the connecting sampling valve group is used for connection and sampling of each of the high-pressure microbial enrichment cultivation kettles, the connecting sampling valve group is connected to the pressurization system, for feeding a liquid or a gas into the high-pressure microbial enrichment cultivation kettles to increase a pressure in the high-pressure microbial enrichment cultivation kettles, making a pressure value in the high-pressure microbial enrichment cultivation kettles consistent with 6 MPa to 20 MPa; and the temperature and pressure sensor group is used to monitor temperature and pressure changes in the high-pressure microbial enrichment cultivation kettles in real time, and send a signal to the control-acquisition terminal;

wherein the connecting sampling valve group comprises a liquid inlet valve, a gas inlet valve, a sampling valve, a gas releasing valve and a liquid outlet valve; wherein:

the high-pressure microbial enrichment cultivation kettles are connected in series through the liquid outlet valve and the liquid inlet valve, the liquid outlet valve of the former high-pressure microbial enrichment cultivation kettles is connected to the liquid inlet valve of the latter high-pressure microbial enrichment cultivation kettles;

the gas inlet valve is used to input gas into the high-pressure microbial enrichment cultivation kettles to increase the pressure in the high-pressure microbial enrichment cultivation kettles, making the pressure value in the high-pressure microbial enrichment cultivation kettles consistent with the actual situation in the deep sea;

the gas releasing valve is used to release the gas in the high-pressure microbial enrichment cultivation kettles to reduce the pressure in the high-pressure microbial enrichment cultivation kettles, and a control terminal thereof is electrically connected to the control-acquisition terminal; and the sampling valve is used to conduct real-time sampling analysis of the microorganisms in the high-pressure microbial enrichment cultivation kettles;

the temperature environment control system comprises a low/high temperature environment system; the isolation and cultivation solid unit and the biological enrichment unit are both disposed in the low/high temperature environment system;

wherein the pressurization system comprises an air compressor, a booster pump, a gas storage tank, a pressure regulating valve and a ventilation pipeline; wherein:

the air compressor, the booster pump, the gas storage tank and the pressure regulating valve are connected in sequence through the ventilation pipeline, and finally are connected to the isolation and cultivation solid unit and the biological enrichment unit in sequence through the ventilation pipeline, for injecting a gas into the isolation and cultivation solid unit and the biological enrichment unit for pressurization; and the pressure regulating valve is used to regulate an internal pressure of the isolation and cultivation solid unit and an internal pressure of the biological enrichment unit; and a control terminal of the air compressor, a control terminal of the booster pump, a control terminal of the pressure regulating valve are all electrically connected to the control-acquisition terminal.

2. The high-pressure environment biological enrichment and solid isolation and cultivation device according to claim 1, wherein the liquid injection module comprises a microflow pump, a liquid injection port and a liquid delivery pipeline; wherein: an input end of the microflow pump is connected to the liquid output end of the biological enrichment unit, and an output end of the microflow pump is connected to the liquid injection port by the liquid delivery pipeline; and the liquid injection port is connected to the microporous nozzle.

3. The high-pressure environment biological enrichment and solid isolation and cultivation device according to the claim 1, wherein the isolation and cultivation chamber is provided with a quick-opening clamp.

4. The high-pressure environment biological enrichment and solid isolation and cultivation device according to the claim 1, wherein a stirring rod is provided on the high-pressure microbial enrichment cultivation kettles; and the stirring rod is used for the high-pressure microbial enrichment cultivation kettles to enhance a reaction process of a substrate during a cultivation process.

5. The high-pressure environment biological enrichment and solid isolation and cultivation device according to claim 1, wherein the device further comprises a movable platform, the isolation and cultivation solid unit, the biological enrichment unit, the pressurization system, the temperature environment control system and the control-acquisition terminal are all disposed on the movable platform, for increasing universality of cultivation scenarios.

6. The high-pressure environment biological enrichment and solid isolation and cultivation device according to claim 2, wherein the isolation and cultivation solid unit is provided with a plurality of the microporous nozzles and a plurality of the solid culture plates; the liquid injection module is connected to each of the microporous nozzles simultaneously; and the solid culture plates are disposed laterally at a bottom of the isolation and cultivation solid unit to realize lateral isolation and cultivation of the microorganisms under conditions of the same temperature and same pressure.

7. The high-pressure environment biological enrichment and solid isolation and cultivation device according to claim 6, wherein the isolation and cultivation chamber is provided with a plurality of connecting partitions in a vertical direction, partitioning the isolation and cultivation chamber into a plurality of connecting cultivation cavities; wherein: a solid culture plate is provided on each of the connecting partitions, and the microporous nozzle is provided inside each of the cultivation cavities; and the liquid injection module is connected to each of the microporous nozzles simultaneously, realizing vertical isolation and cultivation of the microorganisms under conditions of the same temperature and same pressure.

8. The high-pressure environment biological enrichment and solid isolation and cultivation device according to claim 2, wherein the isolation and cultivation solid unit comprises a plurality of the isolation and cultivation chambers, each of the isolation and cultivation chambers is provided with an independent microporous nozzle, an independent solid culture plate and an independent gas injection valve; all of the isolation and cultivation chambers are placed in the same temperature environment control system; and the liquid injection module is connected to the microporous nozzle in each of the isolation and cultivation chambers simultaneously, realizing isolation and cultivation of the microorganisms under conditions of the same temperature and different pressures.

9. The high-pressure environment biological enrichment and solid isolation and cultivation device according to claim 2, wherein the isolation and cultivation solid unit comprises a plurality of the isolation and cultivation chambers, and each of the isolation and cultivation chambers is provided with an independent microporous nozzle, an independent solid culture plate and an independent gas injection valve; each of the isolation and cultivation chamber is placed in an independent temperature environment control system which is correspondingly provided; the liquid injection module is connected to the microporous nozzle in each of the isolation and cultivation chamber simultaneously, and all of the gas injection valves are in communication, realizing isolation and cultivation of the microorganisms under conditions of different temperatures and same pressure.

* * * * *